(12) United States Patent  
Moy et al.

(10) Patent No.: US 9,360,951 B2
(45) Date of Patent: Jun. 7, 2016

(54) WRIST SUPPORT

(71) Applicant: ACCO Brands Corporation, Lincolnshire, IL (US)

(72) Inventors: Brian F. Moy, Wilmette, IL (US); Motokimi Yono, Chicago, IL (US); Andrew A. Monteleone, Chicago, IL (US); Brad L. Schantz, Evanston, IL (US); Christopher H. Cunningham, Mundelein, IL (US)

(73) Assignee: ACCO Brands Corporation, Lake Zurich, IL (US)

( * ) Notice: Subject to any disclaimer, the term of this patent is extended or adjusted under 35 U.S.C. 154(b) by 138 days.

(21) Appl. No.: 14/215,526

(22) Filed: Mar. 17, 2014

(65) Prior Publication Data

US 2014/0263878 A1 Sep. 18, 2014

Related U.S. Application Data

(60) Provisional application No. 61/789,862, filed on Mar. 15, 2013.

(51) Int. Cl.
| | | |
|---|---|---|
| *A47B 21/00* | (2006.01) | |
| *G06F 3/00* | (2006.01) | |
| *A61G 7/075* | (2006.01) | |
| *G06F 3/039* | (2013.01) | |
| *A47B 21/03* | (2006.01) | |
| *G06F 3/0354* | (2013.01) | |
| *A61F 5/058* | (2006.01) | |

(52) U.S. Cl.
CPC ............ *G06F 3/039* (2013.01); *A47B 21/0371* (2013.01); *A61F 5/05841* (2013.01); *A61G 7/075* (2013.01); *G06F 3/03543* (2013.01)

(58) Field of Classification Search
CPC . G06F 3/039; G06F 3/03543; A61F 5/05841; A61G 7/075; A47B 21/0371
USPC ........... 248/118, 918; 128/878; 345/168, 163; 5/646; D24/183, 184
See application file for complete search history.

(56) References Cited

U.S. PATENT DOCUMENTS

| | | | |
|---|---|---|---|
| D239,143 S | 3/1976 | Arluck | |
| D253,568 S | 12/1979 | Brink | |
| 4,270,235 A * | 6/1981 | Gutmann | ............... A61G 7/075 5/646 |
| 4,941,480 A * | 7/1990 | McLean | .............. A61F 5/05841 128/878 |
| D331,042 S | 11/1992 | Hassel et al. | |
| D331,921 S | 12/1992 | Gutke et al. | |

(Continued)

FOREIGN PATENT DOCUMENTS

| | | |
|---|---|---|
| GB | 2364764 B | 8/2004 |
| WO | 00/04489 | 1/2000 |

*Primary Examiner* — Tan Le
(74) *Attorney, Agent, or Firm* — Michael Best & Friedrich LLP

(57) ABSTRACT

A support device for supporting a hand and a wrist of a user includes a body having a hand support portion, a first raised support portion extending from the hand support portion, a second raised support portion spaced apart from the first raised support portion and extending from the hand support portion, and a recess defined at one end by the hand support portion and extending between the first and second raised support portions. The hand support portion is configured to extend across the hand of the user to support the hand. The first and second raised support portions are configured to engage opposing sides of the wrist of the user such that a mid portion of the wrist is suspended above the recess.

24 Claims, 8 Drawing Sheets

(56) References Cited

U.S. PATENT DOCUMENTS

| | | |
|---|---|---|
| D340,990 S | 11/1993 | Kawamura |
| 5,383,632 A | 1/1995 | Shirlin et al. |
| D361,383 S | 8/1995 | Lipson et al. |
| D375,163 S | 10/1996 | Lipson et al. |
| D376,428 S | 12/1996 | Lipson et al. |
| D399,195 S | 10/1998 | Cummings |
| D400,309 S | 10/1998 | Kuntz et al. |
| D407,820 S | 4/1999 | Sullenberger et al. |
| 5,944,289 A | 8/1999 | Speece |
| 6,193,196 B1 | 2/2001 | Hesley |
| D438,725 S | 3/2001 | Takahashi |
| 6,402,100 B1 * | 6/2002 | Rice .................. A47B 21/0371 248/118 |
| 6,454,224 B1 | 9/2002 | Nogueira |
| D470,502 S | 2/2003 | Andrews et al. |
| 6,585,198 B2 | 7/2003 | Dillon |
| D479,719 S | 9/2003 | Kerscher et al. |
| D518,894 S | 4/2006 | Kirn |
| D535,030 S | 1/2007 | Brefka et al. |
| D569,000 S | 5/2008 | Itonaga et al. |
| D603,969 S | 11/2009 | Bauerfeind et al. |
| D608,446 S | 1/2010 | Shibata et al. |
| 7,834,851 B1 * | 11/2010 | Fidali .................. G06F 3/03543 248/118 |
| 7,997,544 B2 | 8/2011 | Fong |
| D698,030 S * | 1/2014 | Crisco ......................... D24/183 |
| D702,841 S | 4/2014 | Wyrozub |
| D710,508 S | 8/2014 | Messer |
| D732,671 S * | 6/2015 | Moy ............................ D24/184 |
| 9,084,704 B2 * | 7/2015 | Oberst .................. A61G 7/075 |
| 9,125,784 B2 * | 9/2015 | Crisco ................ A61G 13/1235 |
| 2003/0169236 A1 * | 9/2003 | Crocker ............. A47B 21/0371 345/168 |
| 2014/0263878 A1 * | 9/2014 | Moy ....................... G06F 3/039 248/118 |

* cited by examiner

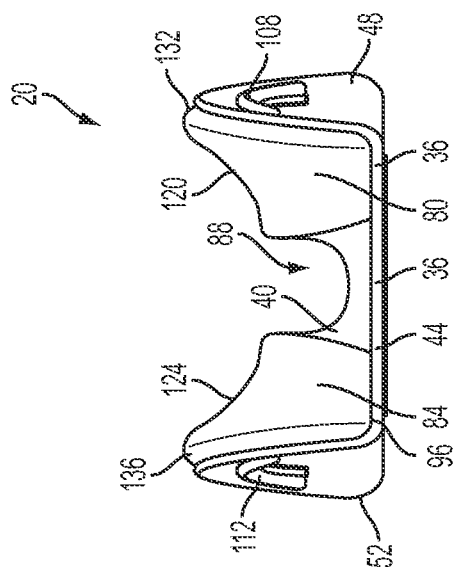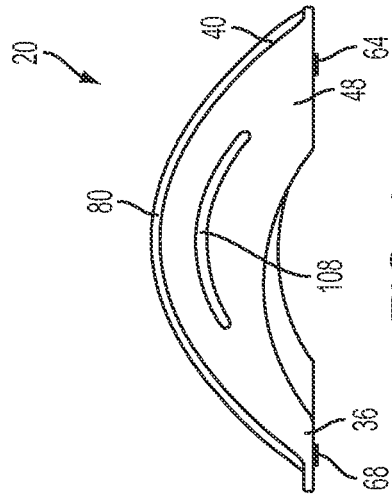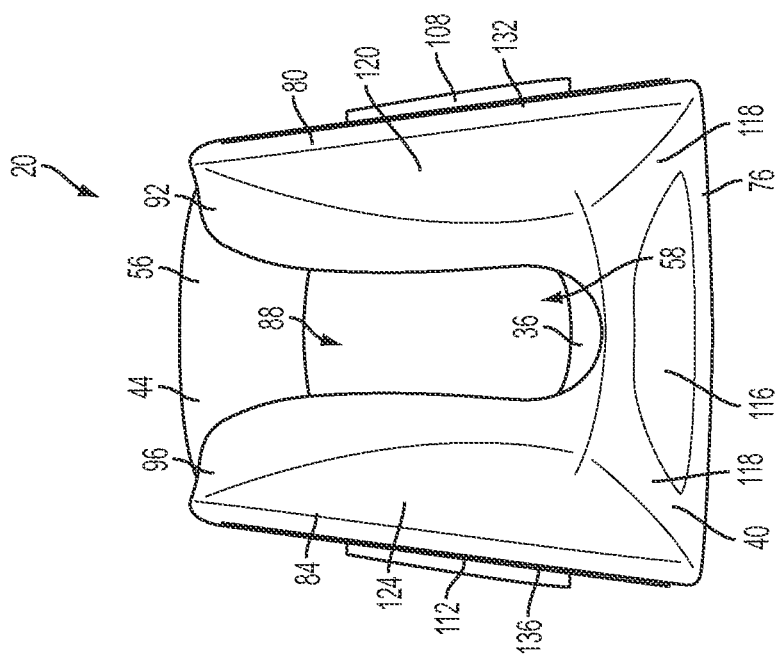

WRIST SUPPORT

CROSS-REFERENCE TO RELATED APPLICATIONS

This application claims priority to U.S. Provisional Patent Application No. 61/789,862, filed Mar. 15, 2013, the entire contents of which are hereby incorporated by reference.

FIELD OF THE INVENTION

The present invention relates to support devices, such as a wrist support for a user's wrist while operating a computer mouse or keyboard.

SUMMARY

In one embodiment, the invention provides a support device for supporting a hand and a wrist of a user. The support device includes a body having a hand support portion, a first raised support portion extending from the hand support portion, a second raised support portion spaced apart from the first raised support portion and extending from the hand support portion, and a recess defined at one end by the hand support portion and extending between the first and second raised support portions. The hand support portion is configured to extend across the hand of the user to support the hand. The first and second raised support portions are configured to engage opposing sides of the wrist of the user such that a mid portion of the wrist is suspended above the recess.

In another embodiment, the invention provides a support device for supporting a hand and a wrist of a user. The support device includes a base having a support surface and a first body removably connectable to the base such that the first body is supported on the support surface. The first body is configured to support a first hand. The support device also includes a second body removably connectable to the base such that the second body is supported on the support surface. The second body is configured to support a second hand that is larger than the first hand. The first body and the second body are alternately connectable to the base.

Other aspects of the invention will become apparent by consideration of the detailed description and accompanying drawings.

BRIEF DESCRIPTION OF THE DRAWINGS

FIG. 2 is a top view of the support device of FIG. 1.

FIG. 3 is an end view of the support device of FIG. 1.

FIG. 4 is a side view of the support device of FIG. 1.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 6:
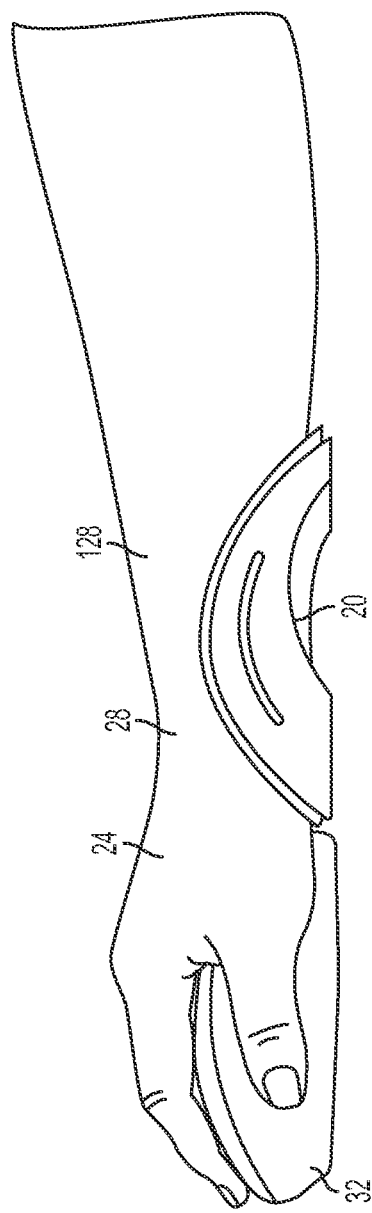
FIG. 6 is a side view of the support device of FIG. 1 supporting a hand and a wrist of a user.

FIGS. 1-4 illustrate a support device 20 for supporting a hand 24 (FIG. 6) and a wrist 28 of a user. The device 20 is designed to support the hand 24 and the wrist 28 when the user is using a computer mouse 32 (as shown in FIG. 6). The device 20 may also be employed to support the hand 24 and the wrist 28 of the user when the user is operating other types of devices, such a computer keyboard.

The illustrated support device 20 includes a base 36 and a body 40. In the illustrated embodiment, the base 36 is composed of a relatively hard material, such as hard plastic, and the body 40 is composed of a relatively soft material, such as a resilient foam or elastic material (e.g., a gel or rubber-like material). In other embodiments, the base 36 may be composed of other suitable materials that can support the body 40. Additionally or alternatively, the body 40 may be composed of other suitable materials to provide comfort and support to the hand 24 and the wrist 28 of the user.

The base 36 is configured to receive and support the body 40. The base 36 includes a bottom wall 44 and two sidewalls 48, 52. The bottom wall 44, the first sidewall 48, and the second sidewall 52 are integrally formed as a single piece and define a support surface 56 (FIG. 7) of the base 36. The bottom wall 44 defines a central opening 58. The first sidewall 48 extends upwardly from a first edge of the bottom wall 44. The second sidewall 52 extends upwardly from a second edge of the bottom wall 44. The sidewalls 48, 52 are spaced apart from each other such that the body 40 is received in an area between the bottom wall 44 and the sidewalls 44, 48.

Figure 5:
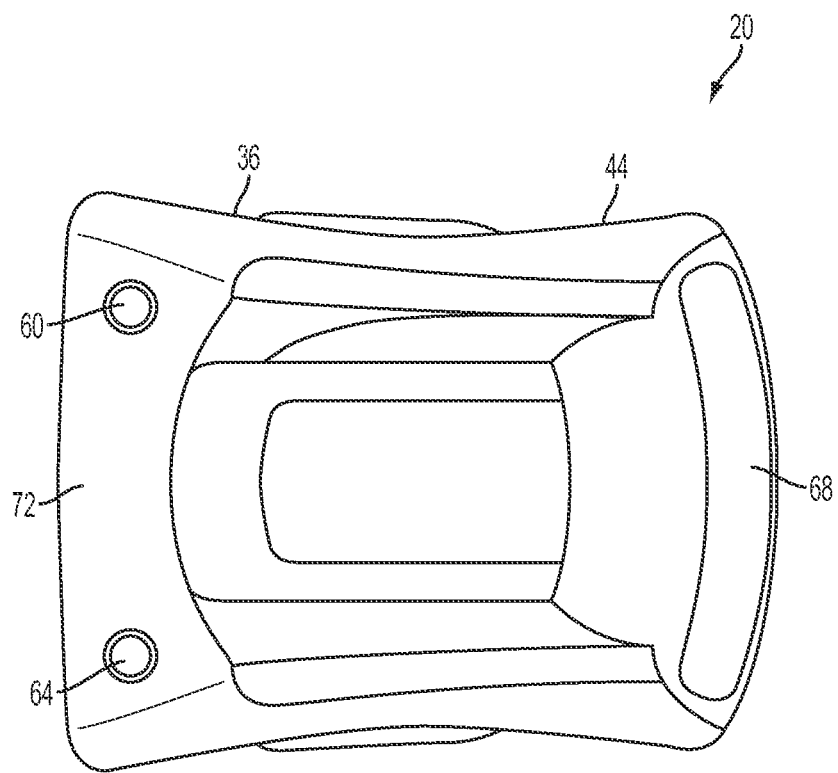
FIG. 5 is a bottom view of the support device of FIG. 1.

As shown in FIG. 5, the base 36 also includes three feet 60, 64, 68 coupled to a lower surface 72 of the bottom wall 44. The lower surface 72 is positioned on a side of the base 36 opposite from the support surface 56. The feet 60, 64, 68 engage a work surface (e.g., a desk, a table, etc.) to support the base 36 on the work surface. Two of the illustrated feet 60, 64 are generally cylindrical and are positioned adjacent a first end of the base 36. The third foot 68 is elongated and curved and is positioned adjacent a second end of the base 36. In the illustrated embodiment, the feet 60, 64, 68 are made of a low-friction material (e.g., nylon or acetal) to facilitate easy sliding across the work surface. In other embodiments, structural features such as rollers (e.g., wheels, balls, cylindrical rollers, etc.) or convex/domed projections could be used to reduce friction.

Referring back to FIGS. 1-4, the illustrated body 40 includes a hand support portion 76, a first raised support portion 80, a second raised support portion 84, and a recess 88. The hand support portion 76, the first raised support portion 80, and the second raised support portion 84 are integrally formed such that the body 40 is a single piece. The first and second raised support portions 80, 84 are spaced apart from each other and extend from the hand support portion 76. The first raised support portion 80 extends from the hand support portion 76 to a first distal end 92. The second raised support portion 84 extends from the hand support portion 76 to a second distal end 96.

The recess 88 is defined at one end by the hand support portion 76 and extends between the first and second raised support portions 80, 84 to separate the raised support portions 80, 84. In the illustrated embodiment, the recess 88 extends entirely through the body 40 such that the distal ends 92, 96 of the raised support portions 80, 84 are separated (i.e., so that no portion of the body 40 directly connects the first distal end 92 to the second distal end 96). The hand support portion 76, the raised support portions 80, 84, and the recess 88 are thereby arranged such that the body 40 is generally U-shaped. The recess 88 is also generally aligned with the central opening 58 in the bottom wall 44 of the base 36 such that a continuous opening is formed through a central portion of the support device 20.

Figure 7:
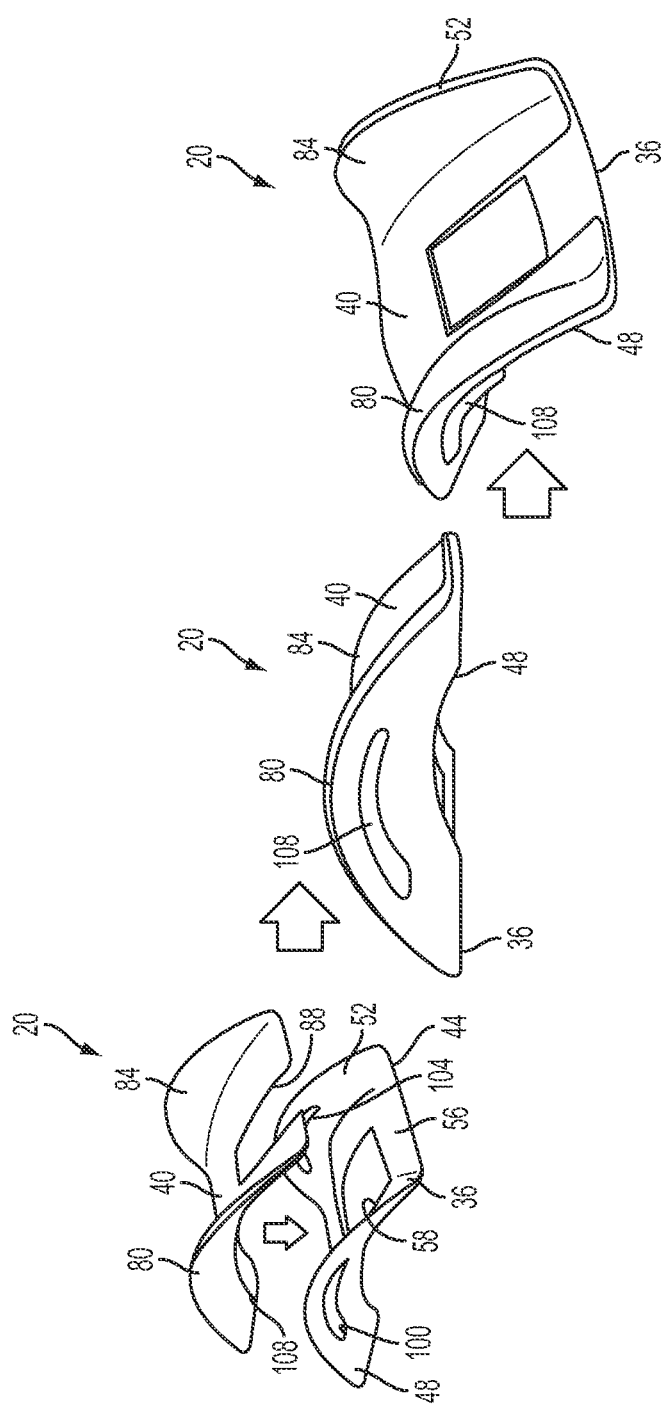
FIG. 7 illustrates a method of connecting a body of the support device to a base of the support device.

When the body 40 is positioned on the base 36 (as shown in FIGS. 1-4), the sidewalls 48, 52 of the base 36 extend along corresponding sides of the raised support portions 80, 84 to provide support to the raised support portions 80, 84. The sidewalls 48, 52 also help connect and secure the body 40 on the base 36. As shown in FIG. 7, each sidewall 48, 52 defines an aperture 100, 104. In the illustrated embodiment, the apertures 100, 104 are elongated and curved slots. A portion of the body 40 extends through each slot 100, 104 to connect the body 40 to the base 36. In the illustrated embodiment, the portions of the body 40 that extend through the slots 100, 104 in the sidewalls 48, 52 are flanges 108, 112 that extend outwardly from the raised support portions 80, 84. The flanges 108, 112 are generally the same shape and size as the slots 100, 104. The resiliency of the material of the body 40 allows a user to remove the body 40 from the base 36 by pulling the flanges 108, 112 out of the slots 100, 104. Similarly, the user can reconnect the body 40 to the base 36 by aligning and pushing the flanges 108, 112 through the slots 100, 104. The flanges 108, 112 frictionally engage inner edges of the base 36 that define the slots 100, 104 to releasably secure the body 40 and the base 36 together.

Figure 1:
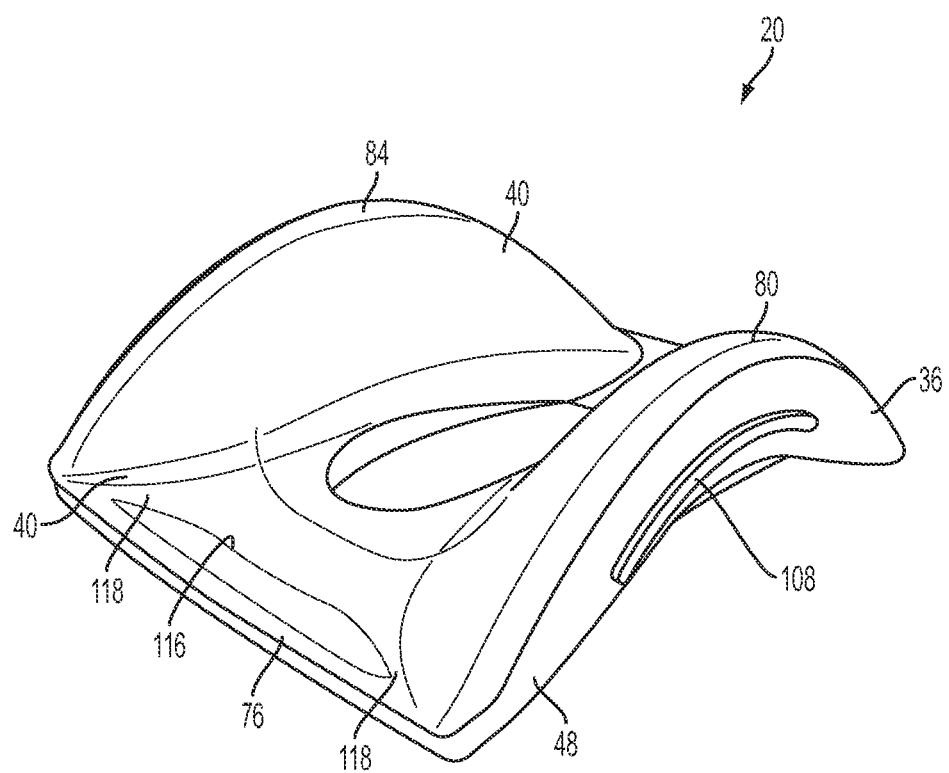
FIG. 1 is a perspective view of a support device embodying the invention.

As shown in FIGS. 1 and 2, the hand support portion 76 of the body 40 is configured (i.e., shaped and sized) to extend across the hand 24 (FIG. 6) of the user. In particular, the hand support portion 76 is configured to extend across the width of the hand 24 at the base of the hand 24 where the hand 24 connects to the wrist 28 (as shown in FIG. 6). In the illustrated embodiment, the hand support portion 76 is contoured to conform to the shape of the base of the hand 24 to provide full support across the base of the hand 24. Specifically, the hand support portion 76 includes a central raised portion 116 and a pair of depressions 118 formed on opposite sides of the central raised portion 116. One depression 118 is configured to receive part of the soft pad at the base of the thumb on the user's hand 24, while the other depression 118 is configured to receive part of the soft pad at the opposite side of the user's hand 24 (i.e., across from the soft pad at the base of the thumb). The central raised portion 116 supports the middle portion of the base of the hand 24 between the two soft pads. The hand support portion 76 is generally symmetrical to conform well to the hand 24 of both left-handed and right-handed users.

As shown in FIG. 3, the first raised support portion 80 includes a first upwardly-facing surface 120, and the second raised support portion 84 includes a second upwardly-facing surface 124. The upwardly-facing surfaces 120, 124 are configured (i.e., shaped and sized) to engage opposing sides of the wrist 28 (FIG. 6) of the user to support the wrist 28. The raised support portions 80, 84 also have sufficient lengths to support a portion of a forearm 128 of the user (as shown in FIG. 6). When the user's wrist 28 is supported on the upwardly-facing surfaces 120, 124, a mid portion of the wrist 28 is suspended above the recess 88 in the body 40 such that nerves and tendons extending through the user's wrist 28 and forearm 128 (i.e., the carpal tunnel area) do not contact any portion of the body 40. As such, the nerves and tendons are not compressed or pinched by any other structure of the support device 20 or of the surrounding environment. The wrist rest 20 is therefore designed to ease and/or prevent carpal tunnel syndrome.

In the illustrated embodiment, the first upwardly-facing surface 120 is inclined from the recess 88 to a first outer edge 132 of the body 40, and the second upwardly-facing surface 124 is inclined from the recess 88 to a second outer edge 136 of the body 40. That is, the upwardly-facing surfaces 120, 124 are generally shorter (i.e., closer to the work surface that supports the device 20) at the recess 88 than at the outer edges 132, 136 of the body 40. The illustrated upwardly-facing surfaces 120, 124 are also curved and, more particularly, at least partially concave in transverse cross-section (i.e., in a direction extending perpendicular to/across the length of the recess 88). In other embodiments, the upwardly-facing surfaces 120, 124 may be inclined and planar.

As shown in FIG. 4, each of the raised support portions 80, 84 is also arch-shaped from the corresponding distal end 92, 96 to the hand support portion 76. That is, the raised support portions 80, 84 are generally taller at mid sections of the raised support portions 80, 84 than at the distal ends 92, 96 or at the hand support portion 76. In the illustrated embodiment, the arch-shape of each raised support portion 80, 84 is generally smooth and continuous along a length of the support portion 80, 84. The arch-shape is designed to follow and support the natural and proper contour of the transition between user's hand 24, wrist 28, and forearm 128. In other embodiments, the arch-shape may be more gradual or more abrupt and/or the arch-shape may not extend along the entire length of each support portion 80, 84.

Figure 8:
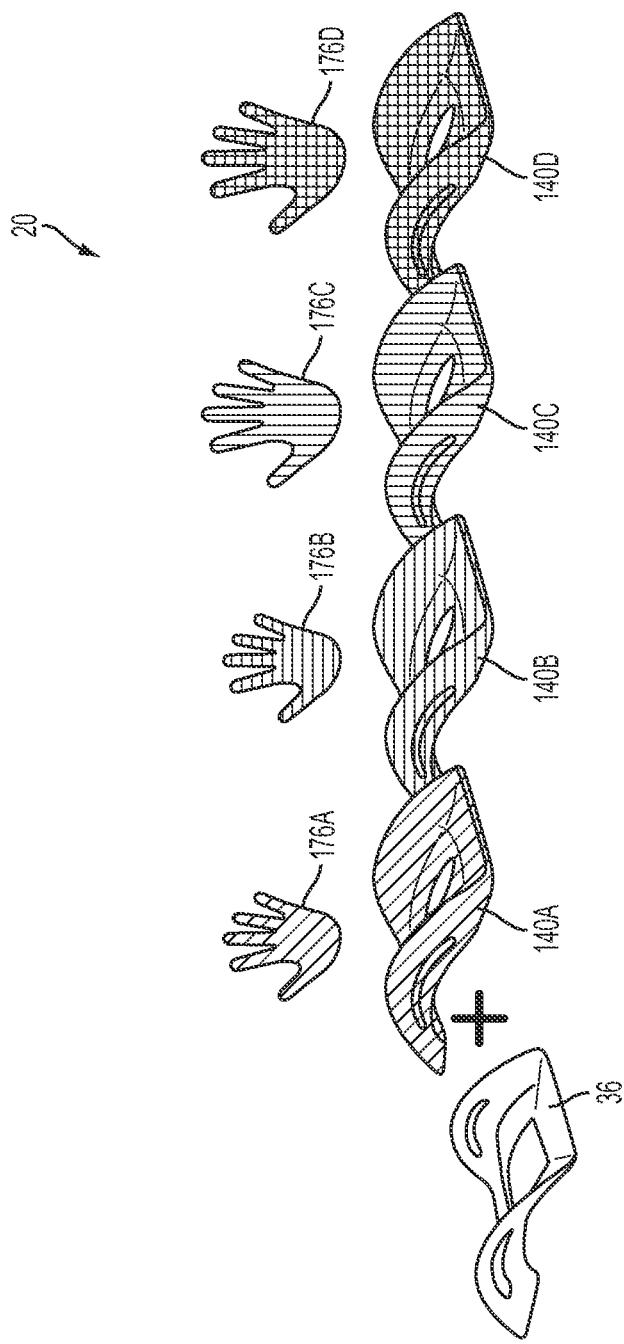
FIG. 8 illustrates a support device including a base and a plurality of different bodies.
Figure 9:
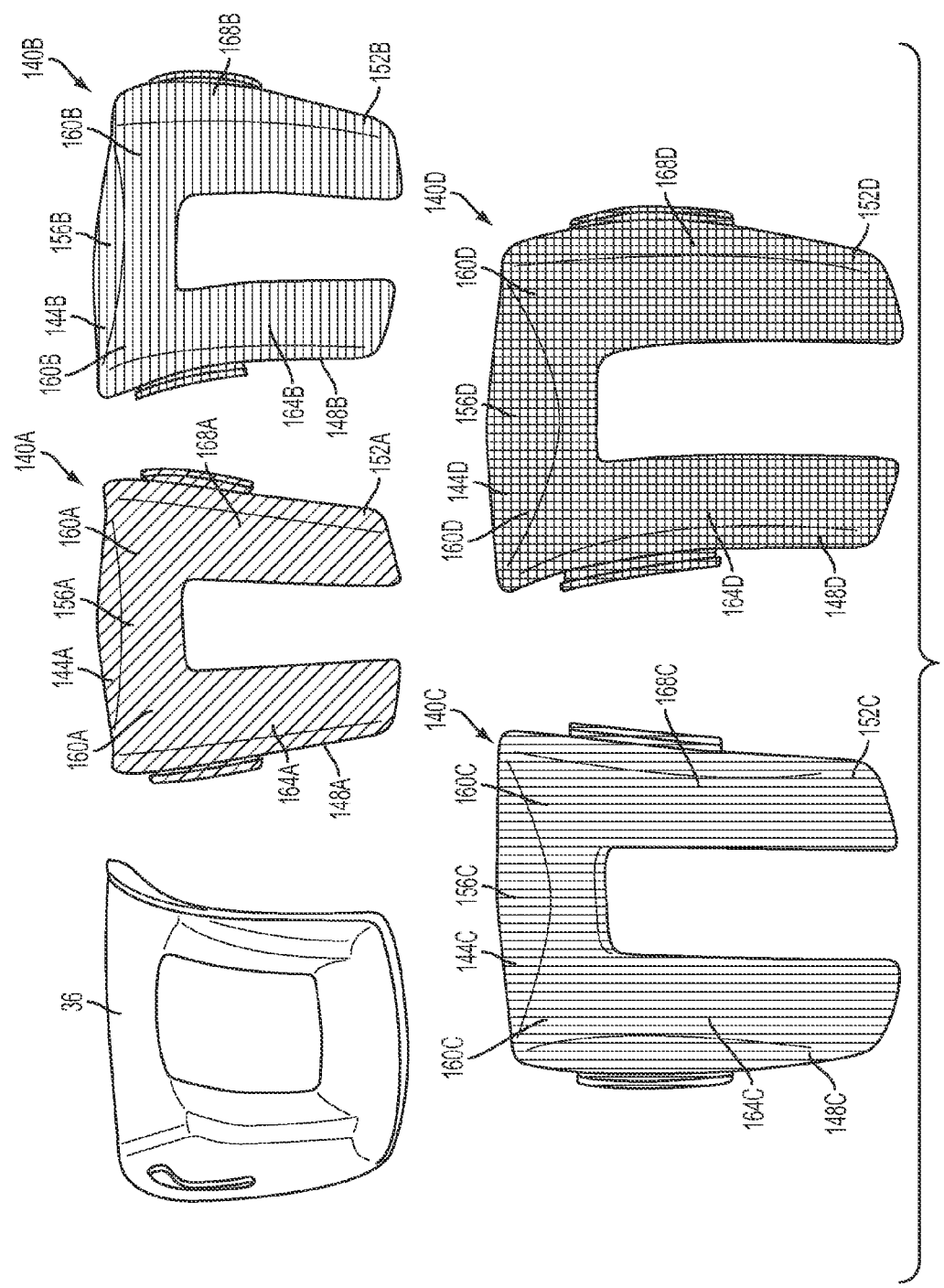
FIG. 9 is a top view of the base and the plurality of different bodies shown in FIG. 8.

FIGS. 8 and 9 illustrate the support device 20 with a plurality of different bodies 140A-D. In the illustrated embodiment, the support device 20 includes the base 36, as described above, and four different bodies 140A-D. The bodies 140A-D are similarly shaped and sized, and each body 140A-D is configured the same as the body 40 described above. However, each of the bodies 140A-D has different contouring than the other bodies 140A-D to support different sized hands 24 and wrists 28 of users. Each of the bodies 140A-D is removably connectable to the base 36 to support a particular size hand 24 and wrist 28. The bodies 140A-D are alternately connected to the base 36 such that only one of the bodies 140A-D is connected to the base 36 at a time. That is, each of the bodies 140A-D needs to be removed from the base 36 before another body 140A-D can be connected to the base 36.

As shown in FIG. 9, each of the bodies 140A-D includes a hand support portion 144A-D and two raised support portions 148A-D, 152A-D extending from the hand support portion 144A-D. Each hand support portion 144A-D includes a central raised portion 156A-D and a pair of depressions 160A-D formed on opposite sides of the central raised portion 156A-D. The sizes (e.g., heights) of the central raised portions 156A-D increases from the first body 140A to the fourth body 140D. That is, the first body 140A includes the smallest central raised portion 156A, the second body 140B includes the second smallest central raised portion 156B, the third body 140C includes the second largest central raised portion 156C, and the fourth body 140D includes the largest central raised portion 156D. Similarly, the sizes (e.g., depths) of the depressions 160D generally increases from the first body 140A to the fourth body 140D. The different sizes of the central raised portions 156A-D and the depressions 160A-D are configured to support relatively larger or smaller hands.

The first and second raised support portions 148A-D, 152A-D include first and second upwardly-facing surfaces 164A-D, 168A-D, respectively. The upwardly-facing surfaces 164A-D, 168A-D have different contouring to accept and cradle wider or narrower wrists and forearms. In particular, the upwardly-facing surfaces 164A, 168A of the first body 140A are contoured to cradle the narrowest wrists and forearms, the upwardly-facing surfaces 164B, 168B of the second body 140B are contoured to cradle the second narrowest wrists and forearms, the upwardly-facing surfaces 164C, 168C of the third body 140C are contoured to cradle the second widest wrists and forearms, and the upwardly-facing surfaces 164D, 168D of the fourth body 140D are contoured to cradle the widest wrists and forearms. In other embodiments, fewer or more bodies configured to support similar or additional sizes of hands, wrists, and forearms may also be usable with the same, single base 36.

Figure 10:
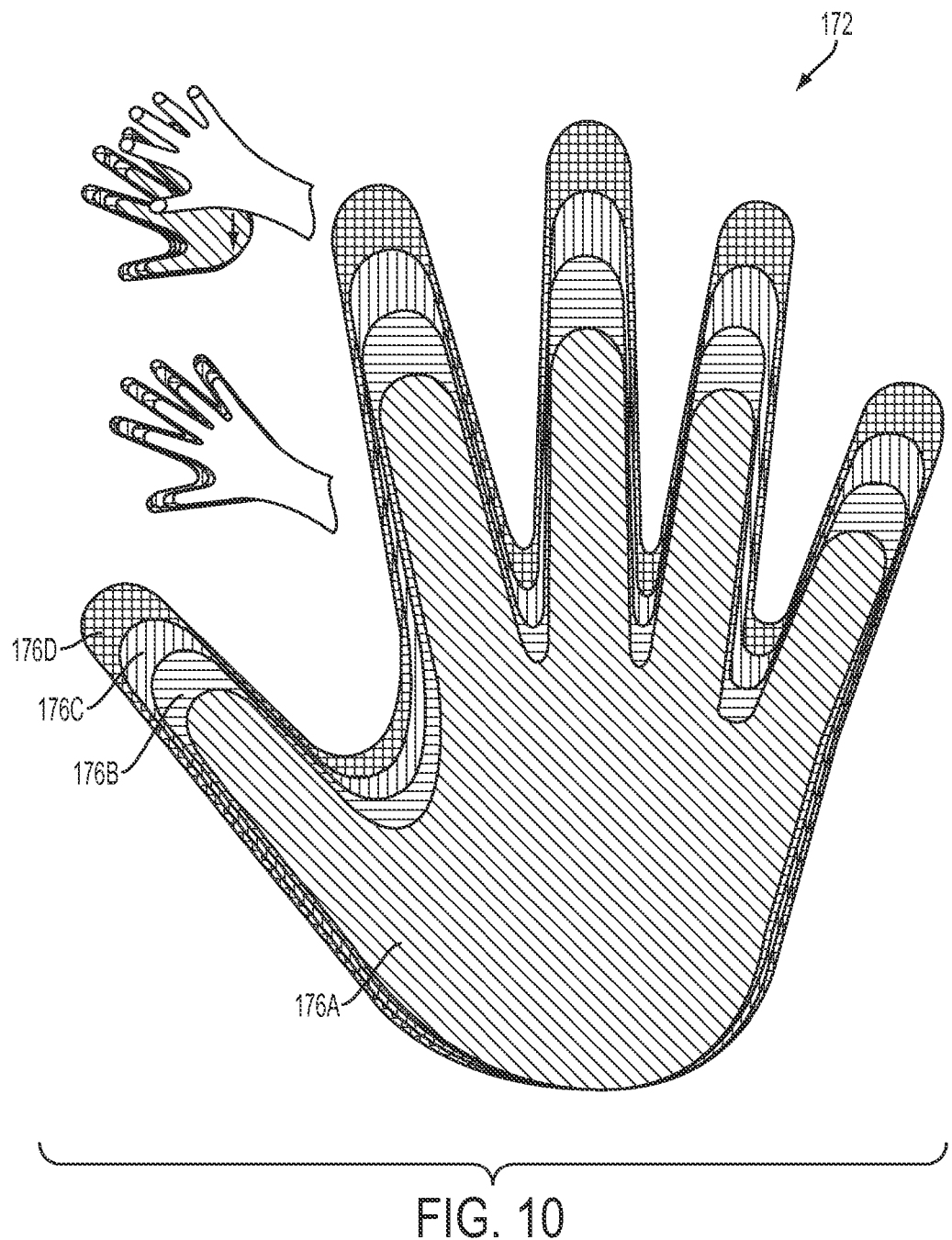
FIG. 10 is a chart for sizing a user's hand with one of the plurality of different bodies shown in FIG. 8.

FIG. 10 illustrates a chart 172 for sizing a user's hand with the different bodies 140A-D shown in FIGS. 8 and 9. The chart includes four handprints 176A-D of different sizes. The first, smallest handprint 176A corresponds to the first body 140A. The second handprint 176B corresponds to the second body 140B. The third handprint 176C corresponds to the third body 140C. The fourth, largest handprint 176D corresponds to the fourth body 140D. In operation, a user places his or her hand on the chart 172 to check which of the handprints 176A-D matches (i.e., is closest in size to) the user's hand. The user then connects the corresponding body 140A-D to the base 36, using the method depicted in FIG. 9. The chart 172 thereby helps the user correctly identify which of the bodies 140A-D to use on the base 36 such that his or her hand 24 and wrist 28 are properly supported by the support device 20.

In the illustrated embodiment, the handprints 176A-D are also color-coded with the bodies 140A-D. That is, the handprints 176A-D drawn on the chart 172 are the same color as the corresponding bodies 140A-D. For example, the first handprint 176A and the first body 140A may both be green, the second handprint 176B and the second body 140B may both be blue, the third handprint 176C and the third body 140C may both be red, and the fourth handprint 176D and the fourth body 140D may both be yellow. Such an arrangement facilitates identifying which body 140A-D corresponds with which handprint 176A-D. In other embodiments, other suitable colors may also or alternatively be employed.

Various features and advantages of the invention are set forth in the following claims.

What is claimed is:

1. A support device for supporting a hand and a wrist of a user, the support device comprising:
a body including a hand support portion, a first raised support portion extending from the hand support portion, a second raised support portion spaced apart from the first raised support portion and extending from the hand support portion, and a recess defined at one end by the hand support portion and extending between the first and second raised support portions;
wherein the first raised support portion extends from the hand support portion to a first distal end, the second raised support portion extends from the hand support portion to a second distal end, and the recess forms an opening through the body such that the first and second distal ends are spaced apart, making the body generally U-shaped when viewed from above;
wherein the first raised support portion is arch-shaped from the first distal end to the hand support portion such that a mid section of the first raised support portion is taller than the first distal end, and the second raised support portion is arch-shaped from the second distal end to the hand support portion such that a mid section of the second raised support portion is taller than the second distal end; and
wherein the hand support portion is configured to extend across the hand of the user to support the hand, and wherein the first and second raised support portions are configured to engage opposing sides of the wrist of the user such that a mid portion of the wrist is suspended above the recess.

2. The support device of claim 1, wherein the first and second raised support portions are spaced apart such that the mid portion of the wrist does not contact any portion of the body when suspended above the recess.

3. The support device of claim 1, wherein the first raised support portion includes a first upwardly-facing surface, wherein the second raised support portion includes a second upwardly-facing surface, and wherein the first and second upwardly-facing surfaces are configured to engage the opposing sides of the wrist.

4. The support device of claim 3, wherein the first upwardly-facing surface of the first raised support portion is inclined from the recess to a first outer edge of the body, and wherein the second upwardly-facing surface of the second raised support portion is inclined from the recess to a second outer edge of the body.

5. The support device of claim 4, wherein the first upwardly-facing surface and the second upwardly-facing surface are both at least partially concave in transverse cross-section.

6. The support device of claim 1, wherein the hand support portion defines a depression that is configured to receive a portion of the hand.

7. The support device of claim 1, further comprising a base connected to the body, wherein the base supports the first raised support portion and the second raised support portion.

8. The support device of claim 7, wherein the body is composed of a relatively soft material, and wherein the base is composed of a relatively hard material.

9. The support device of claim 8, wherein the body is composed of a resilient material, and wherein the base is composed of hard plastic.

10. The support device of claim 7, wherein the base includes a bottom wall extending beneath the hand support portion, a first sidewall extending along a side of the first raised support portion, and a second sidewall extending along a side of the second raised support portion.

11. The support device of claim 10, wherein the bottom wall of the base defines an opening that is generally aligned with the recess of the body.

12. The support device of claim 7, wherein the base defines an aperture, and wherein a portion of the body extends through the aperture to couple the body to the base.

13. The support device of claim 1, wherein the hand support portion, the first raised support portion, and the second raised support portion are integrally formed such that the body is a single piece.

14. A support device for supporting a hand and a wrist of a user, the support device comprising:
a base having a support surface;
a first body removably connectable to the base such that the first body is supported on the support surface, the first body configured to support a first hand; and
a second body removably connectable to the base such that the second body is supported on the support surface, the second body configured to support a second hand that is larger than the first hand;

wherein the first body and the second body are alternately connectable to the base;

wherein each of the first and second bodies includes a hand support portion, a first raised support portion extending from the hand support portion, and a second raised support portion spaced apart from the first raised support portion and extending from the hand support portion; and wherein the first and second raised support portions of the first body include first and second upwardly-facing surfaces, respectively, that are contoured to cradle a first wrist, and wherein the first and second raised support portions of the second body include first and second upwardly-facing surfaces, respectively, that are contoured to cradle a second wrist that is larger than the first wrist.

15. The support device of claim 14, wherein the base includes a first sidewall and a second sidewall that is spaced apart from the first sidewall, and wherein the first body and the second body are alternately received between the first and second sidewalls on the support surface of the base.

16. The support device of claim 14, wherein the base defines an aperture, wherein a portion of the first body extends through the aperture when the first body is connected to the base, and wherein a portion of the second body extends through the aperture when the second body is connected to the base.

17. The support device of claim 16, wherein the aperture in the base is an arcuate slot, and wherein the portions of the first and second bodies that extend through the aperture are flanges corresponding in shape to the arcuate slot.

18. The support device of claim 17, wherein the base includes two arcuate slots on opposite sides of the base, and wherein each body has two flanges corresponding in shape to the two arcuate slots on the base.

19. The support device of claim 14, wherein the hand support portion of the first body includes a first raised portion, wherein the hand support portion of the second body includes a second raised portion, and wherein the second raised portion is generally larger than the first raised portion.

20. The support device of claim 14, wherein each of the first and second bodies also includes a recess defined at one end by the hand support portion and extending between the first and second raised support portions, and wherein the first and second raised support portions are configured to engage opposing sides of a wrist such that a mid portion of the wrist is suspended above the recess.

21. The support device of claim 14, wherein the base is composed of a relatively hard material, and wherein the first and second bodies are composed of relatively soft materials.

22. A support device for supporting a hand and a wrist of a user, the support device comprising:
a base having a support surface;
a first body removably connectable to the base such that the first body is supported on the support surface, the first body configured to support a first hand; and
a second body removably connectable to the base such that the second body is supported on the support surface, the second body configured to support a second hand that is larger than the first hand;
wherein the first body and the second body are alternately connectable to the base;
wherein the base defines an aperture, wherein a portion of the first body extends through the aperture when the first body is connected to the base, and wherein a portion of the second body extends through the aperture when the second body is connected to the base; and
wherein the aperture in the base is an arcuate slot, and wherein the portions of the first and second bodies that extend through the aperture are flanges corresponding in shape to the arcuate slot.

23. The support device of claim 1, wherein the hand support portion includes a central raised portion and a pair of depressions formed on opposite sides of the central raised portion.

24. The support device of claim 7, wherein the body is removably coupled to the base.

* * * * *